(12) United States Patent
Guilloneau et al.

(10) Patent No.: US 9,790,171 B2
(45) Date of Patent: Oct. 17, 2017

(54) SYNTHESIS INTERMEDIATES FOR OBTAINING DERIVATIVES OF SPHINGOSINES, CERAMIDES AND SPHINGOMYELINS WITH GOOD YIELDS

(71) Applicant: M2I DEVELOPMENT, Lacq (FR)

(72) Inventors: Loic Guilloneau, Pau (FR); Samuel Dufour, Orthez (FR); Olivier Guerret, Pern (FR)

(73) Assignee: M2I DEVELOPMENT, Lacq (FR)

( * ) Notice: Subject to any disclaimer, the term of this patent is extended or adjusted under 35 U.S.C. 154(b) by 0 days.

(21) Appl. No.: 14/760,561

(22) PCT Filed: Jan. 14, 2014

(86) PCT No.: PCT/EP2014/050618
§ 371 (c)(1),
(2) Date: Oct. 27, 2015

(87) PCT Pub. No.: WO2014/108564
PCT Pub. Date: Jul. 17, 2014

(65) Prior Publication Data
US 2016/0083335 A1    Mar. 24, 2016

(30) Foreign Application Priority Data

Jan. 14, 2013    (FR) ..................................... 13 00063

(51) Int. Cl.
| | | |
|---|---|---|
| *C07C 233/00* | (2006.01) | |
| *C07C 233/31* | (2006.01) | |
| *C07C 229/08* | (2006.01) | |
| *C07C 231/02* | (2006.01) | |
| *C07C 231/12* | (2006.01) | |
| *C07C 233/47* | (2006.01) | |
| *C07F 7/08* | (2006.01) | |

(52) U.S. Cl.
CPC .......... *C07C 233/31* (2013.01); *C07C 229/08* (2013.01); *C07C 231/02* (2013.01); *C07C 231/12* (2013.01); *C07C 233/47* (2013.01); *C07F 7/0818* (2013.01); *Y02P 20/55* (2015.11)

(58) Field of Classification Search
CPC .................................................... C07C 233/31
USPC ........................................................ 554/39
See application file for complete search history.

(56) References Cited

U.S. PATENT DOCUMENTS 5,220,043 A    6/1993    Dong et al.
7,232,914 B2   6/2007    Katsumura et al.

FOREIGN PATENT DOCUMENTS

| EP | 2308954 A1 | 4/2011 |
|---|---|---|
| WO | WO 94/18289 A1 | 8/1994 |
| WO | WO 2004/010987 A2 | 2/2004 |
| WO | WO 2010/010127 A1 | 1/2010 |

OTHER PUBLICATIONS

Groth et al .: "Asymmetric Synthesis of Derythro-Sphingosine," Tetrahedron, vol. 16/17 , 1991 , pp. 2835-2842.*
Shoyama. et al . : "Total synthesis of sterospecific sphingosine and ceramide , " Journal of Lipid Research, vol. 19, 1978 , pp. 250-259.*
Groth et al., "Asymmetric Synthesis of D-erythro-Sphingosine", Tetrahedron, vol. 47, No. 16/17 (1991), pp. 2835-2842.
International Search Report issued in International Application No. PCT/EP2014/050618 on Apr. 24, 2014.
Shoyama et al., "Total Synthesis of Stereospecific Sphingosine and Ceramide", Journal of Lipid Research, vol. 19 (1978) pp. 250-259.
Bajgrowicz et al., "Synthese Asymetrique D'acides Amines α-Disubstitues," Tetrahedron Letters, vol. 24, No. 35, 1983, pp. 3721-3724, with an English language abstract.
Byun et al., "Synthesis of Sphinogomyelin and Ceramide 1-Phosphate from Ceramide without Protection of the Allylic Hydroxyl Group," Journal of Organic Chemistry, vol. 59, No. 21, 1994, pp. 6495-6498.
Dong et al., "A Useful Synthesis of D-Erythro-Sphingomyelins," Tetrahedron Letters, vol. 32, No. 39, 1991, pp. 5291-5294.
Duclos Jr., "The total synthesis of ganglioside GM3," Carbohydrate Research, vol. 328, 2000, pp. 489-507.
Duffin et al., "Practical syntheses of [13C]- and [14C]-labelled glucosphingolipids," Journal of the Chemical Society, Perkin Transactions 1, 2000 (Published on the web Jul. 3, 2000), pp. 2237-2242.
Hakogi et al., "Synthesis of sphingomyelin sulfur analogue and its behavior toward sphingomyelinase,"Bioorganic and Medicinal Chemistry Letters, vol. 15, 2005 (Available online Mar. 19, 2005), pp. 2141-2144.
Hasegawa et al., "Cross Metathesis Route in Sphingomyelin Synthesis," Chemistry Letters, vol. 33, No. 12, 2004 (Published on web Nov. 13, 2004), pp. 1592-1593.
Koskinen et al., "Sphingosine, an Enigmatic Lipid: A Review of Recent Literature Syntheses,"Synthesis, Aug. 1998, pp. 1075-1091.
Li et al., "Efficient Synthesis of Deuterium- and Tritium-Labeled D-Erythro-Sphingosine," Journal of Labelled Compounds and Radiopharmaceuticals, vol. 42, 1999, pp. 815-826.
Nicolaou et al., "A Practical and Enantioselective Synthesis of Glycosphingolipids and Related Compounds. Total Synthesis of Globotriaosylceramide (Gb3)," Journal of the American Chemical Society, vol. 110, No. 23, 1988, pp. 7910-7912.

(Continued)

*Primary Examiner* — Deborah D Carr
(74) *Attorney, Agent, or Firm* — Birch, Stewart, Kolasch & Birch, LLP

(57) ABSTRACT

The subject matter of the present invention is the novel molecules of formulae E, E' and F. These molecules prove to be synthesis intermediates that are very advantageous for the manufacture of derivatives of sphingosine or of ceramides functionalized in position 1, with good yields, in which $R_1$ and $R_2$ are fatty chains, $R_3$ is an alkyl group and $R_4$ is a protective group for alcohol functions. Another subject of the invention is the use of the intermediates of type F for converting same into intermediates of type G, by means of reduction in the presence of lithium borohydride. The G molecules are precursors that are known to make it possible to obtain sphingolipids or sphingomyelin.

20 Claims, No Drawings

(56) References Cited

OTHER PUBLICATIONS

Oguri et al., "Amino Acids and Peptides, XXIX. A New Efficient Asymmetric Synthesis of α-Amino Acid Derivatives with Recycle of a Chiral Reagent—Asymmetric Alkylation of a Chiral Schiff Base from Glycine," Chemical and Pharmaceutical Bulletin, vol. 26, No. 3, 1978, pp. 803-808.
Solladié-Cavallo et al., "A Four-Step Diastereoselective Synthesis of D-erythro-Sphingosine by an Enantioselective Aldol Reaction Using a Titanium Enolate Derived from a Chiral Iminoglycinate," Journal of Organic Chemistry, vol. 59, No. 11, 1994, pp. 3240-3242.
Spiegel et al., "Sphingolipid metabolism and cell growth regulation," FASEB Journal, vol. 10, Oct. 1996, pp. 1388-1397.
Vo-Hoang et al., "Total Enantioselective Synthesis and in Vivo Biological Evaluation of a Novel Fluorescent BODIPY α-Galactosylceramide," ChemBioChem, vol. 4, 2003, pp. 27-33.
Weis, "New approaches to synthesis of stereospecific sphingomyelin," Chemistry and Physics of Lipids, vol. 102, 1999, pp. 3-12.
Yamada et al., "Asymmetric Synthesis of α-Amino-acid Derivatives by Alkylation of a Chiral Schiff Base," Journal of the Chemical Society, Chemical Communications, Jan. 1, 1976, pp. 136-137.
Yu et al., "Ceramide displaces cholesterol from lipid rafts and decreases the association of the cholesterol binding protein caveolin-1," Journal of Lipid Research, vol. 46, May 1, 2005, pp. 1678-1691.

\* cited by examiner

SYNTHESIS INTERMEDIATES FOR OBTAINING DERIVATIVES OF SPHINGOSINES, CERAMIDES AND SPHINGOMYELINS WITH GOOD YIELDS

SUMMARY

The subject of the present invention is a novel method for the enantioselective synthesis of sphingosine precursors allowing these sphingosines to be obtained with high yields.

TECHNICAL FIELD

Sphingosine is the basic molecule of sphingolipids, one of the two families of hydrolysable lipids. It is composed first of sphingomyelin and secondly of glycolipids such as gangliosides, sulfatides and cerebrosides.

Natural sphingosine (D-erythro sphingosine) has the chemical formula:

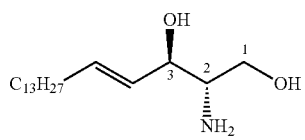

Ceramides are the derivatives of sphingosine amidified on the nitrogen atom at position 2 by fatty acids of variable length and functionalities. The type of fatty acid is dependent on the cells in which the ceramides are contained. Their structures therefore vary as a function of the source (animal or plant) but also as a function of the tissue (skin, muscle, neurone . . . ). Their general formula can be written:

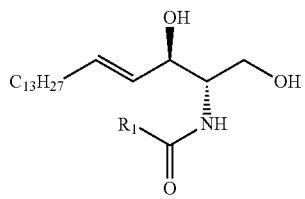

where R1 is a saturated or unsaturated alkyl chain optionally carrying hydroxyl functions or derivatives (e.g. O-acyl ceramide).

From these ceramides, it is possible to gain access to numerous natural compounds by functionalising the primary alcohol. By binding a phosphocholine group, a sphingomyelin is obtained. By binding a phosphate group, a ceramide 1-phosphate is obtained. By creating an ether bridge with an ose, cerebrosides are obtained; and with polysaccharides, gangliosides are obtained (see for example the website: http:www.LipidLibrary.aocs.org).

Discoveries on the therapeutic or cosmetic use of these molecules are numerous since the chemical equilibria between sphingosine, ceramides, sphingosine phosphate, sphingomyelin and sphingolipids govern numerous phenomena such as the management of cholesterol (Dobrowski et al J. of Lipid Research, 2005, p 1678), of muscle inflammation (WO2010010127) or cell growth (The FASEB Journal, 1996, vol. 10, p 1388). The development of the uses thereof in the treatment of some diseases is on the increase (WO2004010987).

There are several pathways to access these molecules. They can be obtained by extraction from plant or animal tissue (EP0689579 B1 or EP 2308954). These methods have the disadvantage of difficult traceability and above all of prohibitive cost for the development of pharmaceutical products which require such traceability (they may be sufficient however for non-food agro-chemical development).

Syntheses (prior to 1991) were described by Devant (see review of sphingomyelin syntheses in: Devant et al, Kontakte, 1992, p. 11). More recently the reviews by Koskinen (Synthesis: 1998, p. 1075) on the synthesis of sphingosines and the review by Weiss (Chemistry and Physics of Lipids, 1999, 102, p 3) on the insertion of phosphocholine chains are representative of the synthesis research carried out to date.

All these pathways have in common the use of sphingosine as ceramide precursor. They therefore require protection of the alcohol at C3 to conduct insertion of the phosphocholine chain. All these syntheses, using sphingosine as intermediate, suffer from several sequences of protection/deprotection to arrive at a protected derivative on the allylic alcohol and able to be functionalised on the primary alcohol (J. Chem. Soc. Perkin Trans I, 2000, p 2237, Duclos Carbohydrate Research, 2000, p 489; Katsumura U.S. Pat. No. 7,232,914 B2).

The total syntheses of ceramide derivatives functionalised at C1, such as sphingomyelin, go through protection/deprotection steps with low yields and as a result the industrial development thereof is difficult.

Only one example describes the insertion of the phosphocholine chain on a non-protected ceramide derivative (Bittmann et al, 1994, JOC, p 6495) leading to N-octanoyl-D-erythro-sphingomyelin with a modest yield (30% for phosphocholine insertion). This insufficiently selective method cannot be applied to long R1 chains. Two other examples by Bittman and Katsumura describe the Insertion of a phosphocholine chain without protection of the allylic alcohol but they are described on N-Boc-sphingosine derivatives in both cases (Katsumura et al. Bioorg. Med. Chem. Lett. 2005, 15, 2141; Katsumura et al. Chem. Lett. 2004, 33, 1592). It is to be noted that Katsumura uses a non-commercial phosphorylation reagent. These access pathways without protection of the allylic alcohol, although original, cannot be envisaged at industrial level.

Shoyama et al (Journal of Lipid Research, vol. 19, 1978, pages 250-259) describe a ceramide intermediate wherein the alcohols are protected and in particular the alcohol at C3 is protected by a $CH(OCOCH_3)C_6H_5$ group. However a said protective group is highly unstable particularly under base conditions, preventing satisfactory functionalization at C1. In addition, the simultaneous use of this group on the alcohol at C3 and of an acetyl group on the nitrogen atom means that the protection steps are little selective (the acetyl possibly grafting itself onto the alcohol or nitrogen indifferently).

From this prior work the applicant has concluded that the selective protection of the alcohol at C3 is essential to ensure good functionalization yields at C1, but to date no truly efficient method exists to allow such functionalizations.

Surprisingly, the applicant has discovered that by having recourse to some novel synthesis intermediates it is possible to simplify the process of synthesising derivatives of ceramides and sphingosines. The pathway through these intermediates allows shortening of the number of steps compared with those hitherto known to the person skilled in the art, and thereby an increase in the total synthesis yields of sphingosine and/or ceramide derivatives functionalized at C1, this being of major interest for the industrial development of these derivatives. These novel intermediates and the method for their synthesis therefore form the subject of the invention. A further subject of the invention is the use of these derivatives to produce different derivative molecules of the sphingosine family (e.g. but not limited thereto sphingosine-1-phosphates), ceramide family (e.g. but not limited thereto sphingomyelin) and natural or functionalized sphingolipids.

DESCRIPTION OF THE INVENTION

The applicant has therefore discovered that the synthesis of novel intermediates of general formula F:

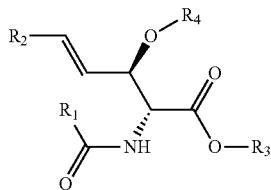

F allows simplification of the methods for synthesising derivatives of sphingosine functionalized at position 1, ceramides functionalized at position 1, sphingomyelin and sphingolipids. These compounds of formula F are characterized by:

$R_1$: a straight-chain or branched aliphatic fatty chain, preferably saturated and of general formula $C_pH_{2p+1}O_r$, where r is an integer between 0 and 3, preferably it is 0 or 1 or 2 and where p is an integer greater than 5, preferably between 8 and 35. R1 may also comprise unsaturations in which case its general formula would be of type $C_pH_{2(p-q)+1}O_r$ where q designates the number of possible unsaturations of the aliphatic chain preferably between zero and 5.

$R_2$: an aliphatic fatty chain of general formula $C_nH_{2n+1}$, n being an integer between 8 and 35, preferably between 10 and 20, more preferably between 10 and 15 and further particularly n=13.

$R_3$: a carbon radical of alkyl, aryl, alkyl-aryl type optionally substituted, preferably R3 is a methyl, ethyl, propyl or iso-propyl radical.

$R_4$: a protective group of alcohol functions such as benzyl, trityl, benzoyl, methoxymethyl, methoxyethyl, tetrahydropyryl groups, or tri-alkyl or akyl-aryl silyl groups such as trimethyl silyl, tert-butyl dimethysilyl, triethyl silyl, tri-isopropyl silyl, tert-butyldiphenyl silyl, dimethylphenyl silyl, triphenyl silyl. Preferably the applicant prefers tri-alkyl silyl groups and more preferably tert-butyl dialkyl silyl groups, in particular the tert-butyl-dimethyl silyl group.

$R_3$ may be a carbon radical of $C_1$-$C_8$ alkyl type, straight-chain or branched, preferably a carbon radical of $C_1$-$C_4$ alkyl type, straight-chain or branched, and optionally substituted, a carbon radical of $C_5$-$C_8$ cycloalkyl type or ($C_6$-$C_{10}$) aryl-($C_1$-$C_8$)alkyl type optionally substituted.

$R_3$ may therefore be a carbon radical of $C_1$ to $C_8$ alkyl type selected from among methyl, ethyl, propyl, butyl, pentyl, hexyl, heptyl or octyl, which may be straight-chain or branched and optionally substituted. Preferably, $R_3$ is a carbon group of $C_1$ to $C_4$ alkyl type selected from among methyl, ethyl, propyl, iso-propyl or butyl which may be straight-chain or branched and optionally substituted.

$R_3$ may also be a carbon radical of aryl type selected from among phenyl, benzyl, tolyl, xylyl or naphthyl, optionally substituted.

In one preferred embodiment the present invention concerns a compound F wherein:

$R_1$: a straight-chain or branched aliphatic fatty chain, preferably saturated and of general formula $C_pH_{2p+1}O_r$, where r equals 0 and where p equals 15.

$R_2$: an aliphatic fatty chain of general formula $C_nH_{2n+1}$, n being an integer of 13.

$R_3$: a methyl, ethyl, propyl or iso-propyl radical.

$R_4$: is a protective group of the alcohol functions: tert-butyl-dimethyl silyl.

A method using the pathway of such intermediates F allows total synthesis yields to be reached of over 15% avoiding the recourse to several protection/deprotection sequences.

These intermediates F are obtained from derivatives E or E' which themselves are also subject of the invention and have the formula:

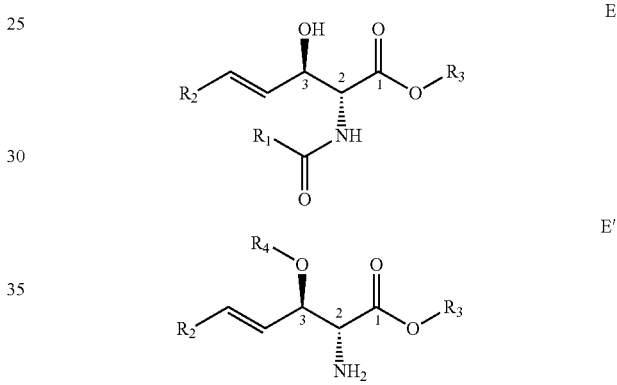

E

E' where $R_1$, $R_2$, $R_3$, $R_4$ have the same meanings as previously.

The following scheme summarises the synthesis steps starting from commercially available aldehydes to reach compounds F, followed by the use of these compounds to synthesise sphingosines, ceramides or sphingomyelins functionalized at position 1 (designated compounds G in the scheme). The use of F to gain access to G is therefore also a subject of the invention since it allows subsequent access to the sphingosine, sphingomyelin or ceramide derivatives functionalized at C1.

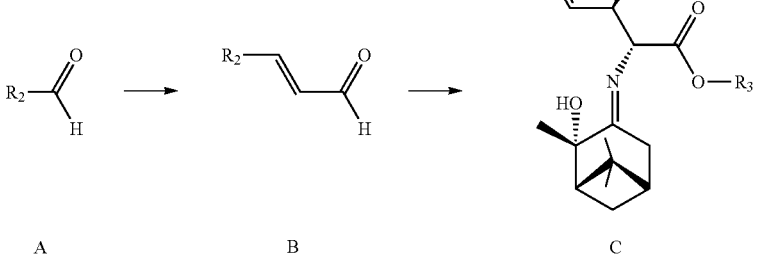

A      B      C

↓

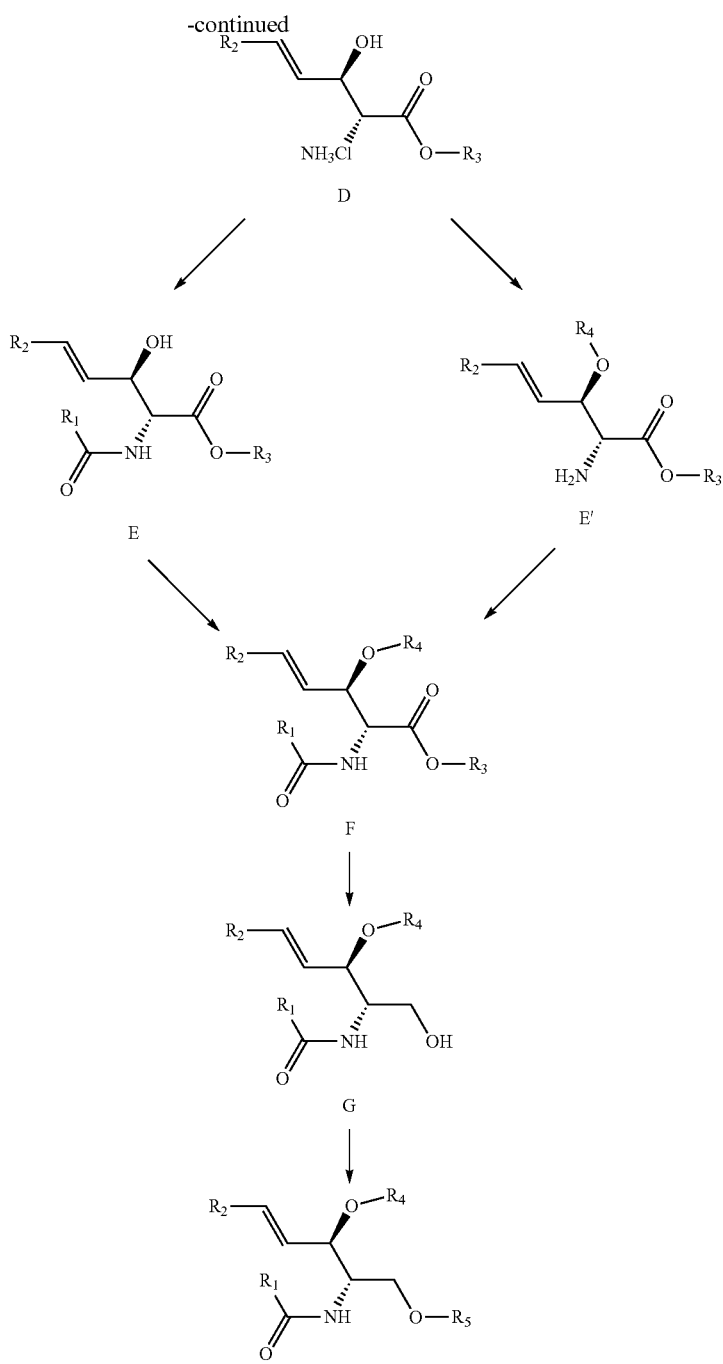

where $R_5$ is a functional group characteristic of the desired sphingolipid. The following table illustrates the correspondence between R5 and the various molecules that the applicant's method is able to obtain.

| Target molecules | Corresponding R5 |
| --- | --- |
| Sphingomyelins | Phosphocholines |
| Ceramide-1-phosphates | -PO3(2-), in the form of lithium, sodium, potassium, calcium or magnesium salt |
| Cerebrosides | Saccharides, galactosides or glucosides (in monomer or oligomer form) |
| Gangliosides | Oligosaccharides functionalized by sialic acid |

Description of the Method for Synthesising E, E' and F Derivatives:

The applicant has discovered 2 manners in which to prepare the F derivatives. The first uses the intermediate E and the second uses the intermediate E'. Preferably the applicant has preference for the pathway using the E Intermediate. The central steps of the invention are therefore the steps from D to F via the intermediates E or E'. For this synthesis route to be of interest it was also necessary to discover a method with which it is possible to progress from commercial aldehydes A to compounds B with good yields. A further subject of the invention therefore concerns the method with which to progress from A to B.

Description of the Non-Inventive Step Allowing A-to-B Operation:

Step 1 to progress from compound A to compound B can be performed in three successive reactions via Horner-Wadsworth-Emmons reaction using a phosphonoacetate to obtain the corresponding unsaturated ester α-β which can then be reduced to allylic alcohol using conventional hydride-based ester-to-alcohol reducing methods. Finally the allylic alcohol thus prepared can be converted to the corresponding aldehyde by means of a mild oxidant such as pyridinium chlorochromate (or PCC) or manganese dioxide (Solladié-Cavallo A.; Koessler. J. K.; J. Org. Chem. 1994, 59, 3240-3242; Schroepfer et al. J. Labelled Cpd. Radiopharm. 1999, 42, 815-826).

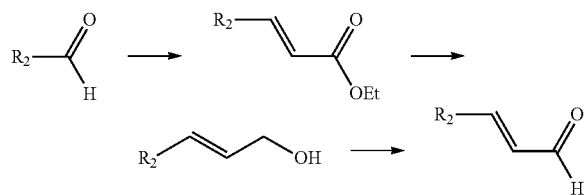

Description of Non-Inventive Step to Progress from B to D:

The second step of the synthesis is designed to avoid the need for an azide which is always problematic when a process undergoes later development onto industrial scale and the only methodology which does not have recourse to a sphingosine intermediate to access ceramide derivatives (Nicolaou, K. C. et al., J. Am. Chem. Soc., 1988, 110, 7910. Zimmermann, P. and Schmidt, R. R. Uebigs Ann. Chem. 1988, 663).

The applicant has therefore chosen a chiral auxiliary: (+)-2-hydroxy-3-pinanone, which can be prepared from pinanediol. Its corresponding iminoglycinate (cf. Shioiri & al. Chem Pharm Bul. 1978, p 803) reacts with B via an aldolization reaction allowing intermediate C to be isolated without purification. This step places the two chiral carbon atoms of sphingosine (C2 and C3). The yield of this step is 91% with high erythro/threo diastereomeric ratio, higher than 95:5, and also with high enantioselectivity. These steps are not new and neither product C nor product D can be claimed as novel as they have been described (S. Yamada, T. Oguri, and T. Shioiri, J. Chem. Soc. Chem. Comm., 1976, 136; Oguri, T.; Kawai, N.; Shioiri, T.; Yamada, S-I, Chem. Pharm. Bull. 1978, 2, 803-808; Bajgrowkcz, J. A et al, Tetrahedron Lett., 1983, 24, 3721-Solladie-Cavallo, A.; Koessler, J. L; J. Org. Chem. 1994, 59, 3240). It is to be noted that the use of the reverse chiral auxiliary, (−)-2-hydroxy-3-pinanone, allows the obtaining of the precursors of the other enantiomer of sphingosine, namely the precursors of L-erythro-sphingosine.

Compound C is then hydrolysed to arrive at molecule D with a yield of 70% (Micouin et al. Chem Bio Chem, 2003, p 27). It is to be noted that this hydrolysis regenerates the chiral auxiliary which can be recycled to reproduce the preceding step. This compound can be converted to sphingosine by simple reduction of the ester function. Unlike the cited authors, the applicant has chosen not to reduce the ester function immediately at position 1 so as to take advantage of the presence of a single hydroxyl function on the backbone of the molecule under construction.

Description of the Step According to the Invention Allowing Progress from D to F Via E or E':

Via E:

The synthesis of E is characterized in that compound D is caused to react on a base preferably of tertiary amine type after which the fatty acid R1C(O)OH is added to the reaction mixture in the presence of a peptide coupling agent e.g. carbodiimides, benzotrialzoles or a mixture of such coupling agents, preferably with the triazole derivative: N,N,N',N'-Tetramethyl-O-(1H-benzotriazol-1-yl)uronium hexafluorophosphate (HBTU) in an aprotic polar solvent such as DMF (dimethyl formamide), THF or preferably a mixture of the two solvents.

The synthesis of F starting from E is characterized in that at a first step E is mixed with a reagent carrying an alcohol function protecting group such as benzyl halide, methoxymethyl chloride (MOM), methoxyethyl chloride (MEM), dihydropyrane (DHP), a trityl derivative, a carboxylic derivative such as benzoyl chloride or silylated derivative such as trimethyl silyl, tert-butyldimethysilyl, triethyl silyl, tri-isopropyl silyl, alkyl aryl silyl: tert-butyldiphenyl silyl, dimethylphenyl silyl, triphenylsilyl, preferably using tert-butyldimethyl silyl chloride as reagent. The reaction is conducted in a polar solvent such as DMF, dichloroethane or acetonitrile, preference being given to DMF, at a temperature ranging from 25 to 90° C. until complete disappearance of the starting product. The reaction is performed in the presence of a non-nucleophilic weak base such as imidazole, triazoles, or alkylamines intended to trap the hydrogen chloride released from the reaction. Preferably the base used is imidazole, pyridine, diisopropylamine, diisopropyl-ethylamine (DIPEA), dimethylaminopyridine (DMAP) or triethylamine.

Via E'

The synthesis of E' starting from D is characterized in that it consists of mixing product D in DMF with at least 2 equivalents, preferably between 2 and 2.2 equivalents of a non-nucleophilic weak base such as imidazole, triazoles or alkylamines intended to trap the hydrogen chloride released from the reaction. Preferably the base used is imidazole, pyridine, diisopropylamine, diisopropyl-ethylamine (DIPEA), dimethylaminopyridine (DMAP) or triethylamine. To the reaction mixture is then added 1 equivalent of a reagent carrying an alcohol function protecting function such as benzyl halide, methoxymethyl chloride (MOM), methoxyethyl chloride (MEM), dihydropyrane (THP), a trityl derivative, carboxylic derivative such as benzoyl chloride or a silylated derivative such as trimethyl silyl, tert-butyldimethysilyl, triethyl silyl, tri-isopropyl silyl, alkyl aryl silyl: tert-butyldiphenyl silyl, dimethylphenyl silyl, triphenylsilyl, preferably using tert-butyldimethyl silyl chloride as reagent.

Starting from E', F is obtained by mixing compound E' with the fatty acid R1C(O)OH in the presence of a peptide coupling agent such as carbodiimides, benzotriazoles or a mixture of such coupling agents, preferably with the triazole derivative: N,N,N',N'-Tetramethyl-O-(1H-benzotriazol-1-yl)uronium hexafluorophosphate (HBTU) in an aprotic polar solvent such as DMF, THF or preferably a mixture of the two solvents.

This step is a key step of our method since on and after this step the synthon F has the hydroxyl at C3 protected in a basic medium and carries an ester function at C1 the reduction of which allows the creation of the primary alcohol function present on the sphingosine and ceramides.

It will be shown further on by the applicant that this particular structure entails special conditions for this reduction. These successive conversions are near-quantitative.

The derivatives of F type are novel and form part of the applicant's invention. This discovery can account for the reason why the person skilled in the art has not managed up until now to maintain the ester functionality at C1 and preferred the reduction thereof before moving onto the following steps.

Description of the Use of F to Access Sphingosines, Sphingomyelins or Ceramides Selectively Functionalized at Position 1:

The silylated ceramide G is obtained by reducing the ester function at C1 with a yield of 90%. In particular, the applicant has discovered that lithium borohydride allows reduction of the ester to a primary alcohol whereas sodium salt even in the presence of lithium chloride (LiCl) reacts only scarcely. The applicant understands this specificity as being due to the chelating nature of the F repeat unit below which, although much hindered by the silyl group, does not prevent the lithium from being chelated by the three nitrogen and oxygen atoms thereby promoting the approaching of the hydride ions to reduce the carboxylic function.

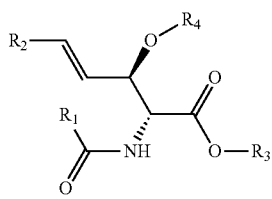

F

Compound G is similar to the intermediates described in the prior art, but the applicant claims an access to this synthon in only 6 steps. As for the F intermediates, these are original and carry the signature of the simplicity of the synthesis strategy discovered by the applicant and therefore form one of the subjects of the invention.

The subsequent steps are not original since described in several documents and do not form part of the invention. However, to compare the work in the prior art with this new synthesis method, the global syntheses of the sphingosine derivatives led to yields of between 15 and 30% from the starting aldehyde.

Among the different targeted sphingolipids, they all have as starting synthon ceramide G which is functionalized using different pathways. Ceramide-1-phosphate is simply obtained in two steps by reacting G on $POCl_3$ then de-protecting the allylic alcohol. Sphingomyelin is obtained from G as in U.S. Pat. No. 5,220,043 or according to Dong; J. A. Butcher; Tetrahedron Letters 1991, 32, 5291 in 3 steps.

EXAMPLES

Analyses by nuclear magnetic resonance were conducted using a Brucker 400 MHz spectrometer. The chemical shifts' are indicated for each product characterized in relation to the resonance frequencies of each atom ($^1H$ or $^{13}C$).

Reaction monitoring and product identification were performed by thin layer chromatography (Merck, TLC silica gel 60 $F_{254}$) or alternatively by HPTLC (HPTLC silica gel 60 $F_{254}$) using a CAMAG sampler (Automatic TLC sampler 4) for accurate measurements of substrate concentration or possible impurities.

GC monitoring was performed on GC-FID apparatus, HP 5890 series II mounted by an HPS column (30 m×0.53 mm×0.88 um).

I.R. data were recorded on FT-IR, spectrum one apparatus by PerkinElmer.

The melting points were recorded on electothermal equipment.

For Examples N° to 1 to 6: n=13, p=23 and q=0.

Examples 1 to 6 show that starting from tetradecaldehyde, it is possible to prepare sphingomyelin which is a ceramide functionalized at C1 by a phosphocholine group. Example 4 is used to compare the pathway which would use synthesis via sphingosine which requires 2 additional steps, clearly evidencing the advantages of Example 6 whereby sphingomyelin is obtained directly via E and F.

Example 1: Synthesis of 2-e-Hexadecenal (from A to B) According to the Prior Art 1-Tetradecanal (Compound A where n=13)

The tetradecanal used in this example was either purchased from Boc Science (85% purity) or prepared following the protocol described in: De Luca, L; Giacomelli, G.; Porcheddu, A. *Org. Lett.* 2001, 3, 3041-3043; O'Doherty et al. *J. Org. Chem,* 2006, 71, 6686-6689.

Synthesis of ethyl 2-Hexadecenoate

To a suspension of sodium hydride (2.4 g, 58.85 mmol) in anhydrous THF (40 mL), the dropwise addition was made of triethyl phosphonoacetate (9.4 mL, 47.08 mmol) at 0° C. After an agitation time of 30 minutes at 0° C., the tetradecanal (10.0 g, 47.08 mmol) in solution in anhydrous THF (40 mL) was added at once and the reaction medium left to return to ambient temperature. The reaction was quenched through the addition of saturated NaCl solution (50 mL). The aqueous phase was extracted with diethyl ether (3×200 mL). The organic phases were combined, dried over $MgSO_4$, filtered and concentration in vacuo. The reaction product was purified on a silica column (Heptane/AcOEt: 95:5) leading to a colourless liquid (12.3 g; 92%).

Rf=0.24 (Hexane/$Et_2O$: 95:5).

CPG: $t_R$=13.13 min (triethylphosphonoacetate); $t_R$=15.80 min (1-tetradecanal); $t_R$=20.60 min (ethyl 2-Hexadecenoate).

$^1H$ NMR (400 MHz, $CDCl_3$): 0.87 (t, 3H, $CH_3$); 1.25 (br, 20H); 1.28 (t, 3H, $CH_3$); 1.44 (m, 2H, $CH_2$); 2.18 (qd, 2H, CH2, $^3J$=6.5 Hz, $^4J$=1.5 Hz); 4.18 (q, 2H, $CH_2$); 5.80 (dt, 1H, $^3J$=15.5 Hz, $^4J$=1.5 Hz); 6.96 (dt, 1H, $CH_2$, $^3J$=15.5 Hz, $^3J$=6.5 Hz).

2-e-Hexadecen-1-ol

DIBAl-H (54.5 mL, 1 M in cyclohexane, 2.4 equiv) was added dropwise at 0° C. to a solution of ethyl hexadecenoate (6.4 g, 22.66 mmol) in anhydrous THF (20 mL). The system was placed under agitation at 0° C. and the progress of the reaction was monitored by TLC. Diethyl ether (50 mL) and a saturated aqueous solution of sodium tartrate (50 mL) were successively added and agitation maintained until two separate phases could be observed. The aqueous phase was extracted with diethyl ether (2×50 mL). The organic phases were combined, dried over $MgSO_4$ and concentrated in vacuo leading to a white wax (5.3 g; 97%).

Rf=0.31 (Hexane/$Et_2O$: 1:1).

CPG: $t_R$=19.1 min $^1H$ NMR (400 MHz, $CDCl_3$): 0.87 (t, 3H, $CH_3$); 1.25 (br, 22H); 2.03 (q, 2H, CH2, $^3J$=6 Hz); 4.09 (d, 2H, $^3J$=5 Hz); 5.66 (m, 2H).

2-e-Hexadecen-1-al (Compound B)

To a solution of 2-€-Hexadecen-1-ol (5.2 g; 21.63 mmol) in 30 mL anhydrous $CH_2Cl_2$, were added at 0° C. PCC (16.3 g; 43.26 mmol) in suspension in 30 mL $CH_2Cl_2$ and Clarcel (20 g). After an agitation time of 3 h at 0° C., the mixture was diluted with 20 mL ether then filtered on silica. The filtrate was concentrated and the reaction product purified on a silica column (Heptane/AcOEt: 95:5) leading to a white solid (2.86 g; 55%).

Rf=0.14 (Hexane/$Et_2O$: 95:5)
CPG: $t_R$=18.9 min
$^1H$ NMR (400 MHz, $CDCl_3$): 0.88 (t, 3H, $CH_3$); 1.26 (br, 20H); 1.50 (m, 2H, $CH_2$); 2.35 (qd, 2H, $^3J$=7 Hz, $^4J$=1.5 Hz); 6.1 (ddt, 1H, $^3J$=15.5 Hz, $^3J$=8 Hz, $^4J$=1.5 Hz); 6.85 (td, 1H, $^3J$=15.5 Hz, $^3J$=7 Hz); 9.5 (d, 1H, $^3J$=8 Hz).

Example 2 from B to D

(1R,2R,3S,5R)-(−)-Pinanediol

A 250 mL three-necked round-bottom flask was charged with S-(−)-α-pinene (24.3 g; 178.37 mmol), potassium osmate dihydrate (0.36; 132 mg), N-oxide-N-methylmorpholine (60% in water; 214.04 mmol; 41.7 g) dissolved in 17.3 mL pyridine, 107 mL acetone and 11.9 mL deionised water. The mixture was heated under reflux for 60 hours. The reaction was then diluted through the addition of 300 mL MTBE and 60 mL hexane. 200 mL of water were added and the organic phase decanted, washed with 10% citric acid solution (this operation was conducted with 3 times 100 mL citric solution), saturated aqueous $NaHCO_3$ solution (100 mL), brine (100 mL), dried over $MgSO_4$ and concentrated in vacuo leading to a dark orange oil (24.5 g).

CPG: $t_R$=12.0 min (diol); $t_R$=10.9 min (1R,2R,5R)-(+)-2-hydroxy-3-pinanone; 5 to 10%)

(1R,2R,5R)-(+)-2-hydroxy-3-Pinanone

To a solution of diol (24.5 g; 143.9 mmol) in 154 mL of DMSO/$CH2Cl_2$ mixture (1:1), triethylamine (80.2 mL; 575.6 mmol) was added at 10° C. The $SO_3$.Pyridine complex (68.7 g; 431.72 mmol) was then added portion-wise in 30 minutes whilst maintaining the temperature below 20° C. The mixture was left under agitation for 2 hours at 10° C. then diluted with 300 mL AcOEt. The organic phase was washed with 0.5 N HCl solution (2*150 mL), brine (150 mL), dried over $MgSO_4$ and concentrated in vacuo leading to a brown-orange oil. The reaction product was purified on a silica column (Mecyclohexane/AcOEt: 9:1) leading to a yellow oil (19.2 g; 63% in two steps).

CPG: $t_R$=10.9 min;
$^1H$ NMR (400 MHz, $CDCl_3$): 0.90 (s, 3H); 1.30 (s, 3H); 1.40 (s, 3H); 1.70 (d, 1H, J=12.0 Hz); 2.10 (m, 2H); 2.30 (s, 1H); 2.50 (m, 1H); 2.60 (brs, 2H).

Synthesis of (1R,2R,5R)-ethyl-((2-hydroxypinan-3-ylene)amino)acetate (Compound C)

A 250 mL single-neck flask was charged with ethyl glycinate hydrochloride (16.6 g; 118.9 mmol) in suspension in 100 mL distilled toluene. Gaseous ammonia was bubbled through the reaction medium for 1 hour. The generated ammonium chloride was removed by simple filtration. To the filtrate was added (1R,2R,5R)-(+)-2-hydroxy-3-pinanone (10.0 g; 59.4 mmol) and a few drops of boron trifluoride etherate ($BF_3.OEt_2$). The system equipped with a Dean-Stark was heated under reflux for 5 hours and the mixture then concentrated in vacuo.

The reaction product can be purified on a silica column pre-impregnated with triethylamine (5% in ether) and eluted with ethyl ether, distilled or used as such at the following step.

Rf=0.35 (Cyclohexane/AcOEt: 1:1)
$^1H$ NMR (400 MHz, $CDCl_3$): 0.88 (s, 3H, $CH_3$); 1.30 (t, 3H, $CH_3$, =7.0 Hz); 1.34 (s, 3H, $CH_3$); 1.53 (s, 3H, $CH_3$); 1.57 (d, 1H, J=10.0 Hz); 2.07 (m, 2H); 2.36 (dtt, 1H, J=10.0 Hz; J=6.0 Hz; J=1.5 Hz); 2.50 (d, 2H, J=1.5 Hz; J=1.0 Hz); 2.61 (s, 1H, OH); 4.17 (s, 2H, =N—$CH_2$); 4.23 (q, 2H, $CH_2$ $CH_3$, J=7.0 Hz).
$^{13}C$ NMR (100 MHz, $CDCl_3$): 180.0 (C-1 quat. Ester); 170.2 (C-1' quat. Amide); 76.5 (C-2' quat.); 60.9 ($\underline{CH_2}$—$CH_3$); 52.6 (C-2); 50.4 (C-3'); 38.6 (C quat); 38.3 (C-5); 33.7 (C-6); 28.2 ($CH_3$); 28.1 (C-4'); 27.3 ($CH_3$); 22.8 ($CH_3$); 14.2 ($CH_2$—$\underline{CH_3}$).

(1R,2R,5R)-ethyl-((2-hydroxypinan-3-ylene)amino)acetate (5.0 g; 19.88 mmol) was dissolved in 9.6 mL anhydrous $CH_2Cl_2$. The system, placed in an argon atmosphere, was cooled to 0° C. Titanium chloride isopropoxide (5.2 g; 19.88 mmol) in solution in 15.3 mL anhydrous $CH_2Cl_2$, 2-€-Hexadecen-1-al (3.7 g; 15.53 mmol) in solution in 7.7 mL anhydrous $CH_2Cl_2$ and anhydrous triethylamine (4.8 mL; 34.17 mmol) were successively added at 0° C. The reaction medium was held for 4 hours at 0° C. then quenched through the addition of brine solution (25 mL). The aqueous phase was extracted with ethyl acetate, dried over $MgSO_4$ and concentrated in vacuo giving an orange-yellow oil (9.7 g, 100%) (73:27 mixture of isopropyl and ethyl ester).

Rf=0.7 (Cyclohexane/AcOEt: 1:1)
$^1H$ NMR (400 MHz, $CDCl_3$): 0.88 (t, 3H, J=6.5 Hz); 1.50-1.10 (m, 28H, ($CH_2$)$_{12}$+2$CH_3$); 1.50 (s, 3H, $CH_3$); 1.53 (d, 1H); 2.13 (q, 2H); 2.18-1.95 (m, 2H); 2.34 (dtd, 1H); 2.51 (m, 1H); 3.25 (s, 1H); 3.75 (s, 1H); 4.15 (d, 1H, J=6.7 Hz); 4.20 (dt, 1H, J=7.0 Hz; J=4.0 Hz); 4.55 (t, 1H, J=6.7 Hz); 5.05 (hept, 1H, J=6.3 Hz, $\underline{CH}$($CH_3$)$_2$); 5.55 (dd, 1H, J=15.4 Hz; J=7.1 Hz); 5.70 (dt, 1H, J=15.4 Hz; J=6.5 Hz).
$^{13}C$ NMR (100 MHz, $CDCl_3$): 180.4 (C-1' quat. Ester); 170.0 (C-1 quat amide); 134.6 (C-5); 127.8; 76.7; 73.8; 68.9 ($\underline{CH}$($CH_3$)$_2$); 67.3; 50.2; 38.6; 38.5; 34.3; 28.4 ($CH_3$); 28.1; 27.4 (CH3); 22.8 ($CH_3$); 34.3-32.4; 32.1; 29.8; 29.5; 29.4; 29.2; 23.0; 22.9; 21.9 (C-6 to C-17, $CH(CH_3)_2$); 14.3.

To a solution of the aldolization crude (9.7 g) in THF (34 mL) was added dropwise an aqueous 1.2 M HCl solution (133 mL). The mixture was left under agitation 72 hours at ambient temperature. The white precipitate formed as and when the reaction progressed was filtered to give 3.0 g of ester hydrochloride (compound D) (50% over the 2 steps). Extraction of the aqueous phase with ethyl acetate allows recycling of the (1R,2R,5R)-(+)-2-hydroxy-3-pinanone.

Example 3: Synthesis of Sphingosine and Ceramide According to the Prior Art D-erythro-sphingosine The aminoester hydrochloride D (2.2 g; 5.82 mmol) was placed in suspension in 40 mL of EtOH/water mixture (3:1). To this suspension was added sodium borohydride (7.10 g; 187.7 mmol). The system was left under agitation 72 hours at 0° C. The reaction was treated through the addition of saturated $NH_4Cl$ solution (40 mL). The aqueous phase was extracted with $CH_2Cl_2$ (4 extractions with 100 mL of this solvent), washed in brine, dried over $MgSO_4$, filtered and concentrated in vacuo leading to sphingosine in the form of a white solid (1.5 g; 86%).

Rf=0.3 ($CHCl_3$/MeOH/$H_2O$: 13:6:1)
mp=79-82° C.
$^1H$ NMR (400 MHz, $CDCl_3$): 0.90 (t, 3H, J=6.5 Hz); 1.50-1.20 (m, 22H, ($CH_2$)$_{12}$); 2.00 (q, 2H, J=7.8 Hz); 3.15

(s, 1H, OH); 3.70 (m, 4H); 4.30 (s, 1H, OH); 5.40 (dd, 1H, J=15.5 Hz; J=6.3 Hz); 5.80 (dt, 1H, J=15.5 Hz; J=7.8 Hz).
$^{13}$C NMR (100 MHz, CDCl$_3$): 134.5; 129.2; 74.4; 63.1; 56.4; 32.6; 32.1; 29.8; 29.5; 22.8 (C-6 to C-17); 14.2 (C-18).

N-palmitoyl-D-erythro-sphingosine (Ceramide)

To a suspension of HBTU (1.4 g; 3.67 mmol) in DMF (7 mL) were successively added palmitic add (0.86 g; 3.34 mmol) and D-erythro-sphingosine (1.0 g; 3.34 mmol) in solution in THF (45 mL). The white suspension obtained was cooled to 0° C. and triethylamine (1.1 mL; 8.04 mmol) was added. The reaction medium was left under agitation 12 hours at ambient temperature after which a 5% aqueous citric add solution (20 mL) was added. The suspension was filtered and the white solid obtained re-dissolved in water (30 mL) at ambient temperature. The white suspension was filtered, washed with water and vacuum dried for 12 hours at 40° C. which gave N-palmitoyl-D-erythro-sphingosine (1.6 g; 90.0%).
$^1$H NMR (400 MHz, CDCl$_3$): 0.97 (6H, t); 1.10-1.40 (m, 46H); 1.62 (2H, m); 2.04 (2H, m, C$\underline{H_2}$—CH); 2.21 (t, 2H, J=8.2 Hz, C$\underline{H_2}$CONH); 2.71 (m, 2H); 3.69 (m, 1H); 3.80-4.00 (m, 2H); 4.28 (m, 1H, C$\underline{H}$(OH)CH); 5.52 (ddt, 1H, J=15.4 Hz; J=6.4 Hz; J=1.0 Hz, CH(OH)C$\underline{H}$); 5.77 (dtd, 1H, J=15.4 Hz; J=6.7 Hz; J=1.1 Hz, C$\underline{H_2CH}$); 6.22 (d, 1H, J=6.8 Hz, NH).

Example 4, Non-Inventive: Synthesis of Ceramide Protected at C3 Starting Solely from Example 3 According to the Prior Art (Compound G)

Synthesis of 3-O-Benzoyl-N-Palmitoyl-D-erythro-sphingosine Protection at C1

A solution of N-palmitoyl-D-erythro-sphingosine (0.58 g, 1.08 mmol), triethylamine (1.2 ml), DMAP (5 mg) and trityl chloride (0.45 g, 1.62 mmol) in CH$_2$Cl$_2$ (14 mL) was refluxed for 60 h. The reaction medium was then concentrated in vacuo and re-dissolved in 30 mL of ethyl acetate. The organic phase was washed with aqueous 1N HCl solution (30 mL), saturated aqueous NaHCO$_3$ solution (30 mL) and brine (30 mL), dried over MgSO$_4$ and concentrated in vacuo. The residue was purified by chromatography on silica gel (Heptane/AcOEt: 7:3) leading to N-palmitoyl-1-O-trityl-D-erythro-sphingosine (0.39 g, 46%).
Rf=0.49 (CH$_2$Cl$_2$/EtOAc/Et$_3$N: 97:3:0.1).
$^1$H NMR (400 MHz, CDCl$_3$: 0.88 (6H, t), 1.40-1.15 (46H, m), 1.64 (2H, m), 1.91 (2H, m), 2.20 (2H, t, J=8.2 Hz), 3.28 (1H, dd, J=9.6 Hz, J=4.0 Hz), 3.40-3.35 (2H, m), 4.04 (1H, m), 4.17 (1H, m), 5.24 (1H, dd, J=15.4 Hz, J=6.2 Hz), 5.62 (1H, dt, I=15.4 Hz, J=6.6 Hz), 6.06 (1H, d, J=7.5 Hz, NH), 7.35-7.20 (9H, m), 7.35-7.45 (6H, m).
Protection at C3
To a solution of N-Palmitoyl-1-O-trityl-D-erythro-sphingosine (0.39 g, 0.50 mmol) in pyridine was added DMAP (10 mg) followed by benzoyl chloride (0.1 ml, 0.85 mmol). The system was left under agitation 20 hours at ambient temperature, concentrated in vacuo and re-dissolved in ethyl acetate (25 mL). The organic phase was washed with saturated aqueous NaHCO$_3$ solution (30 mL), washed with brine (30 mL), dried over MgSO$_4$, filtered and concentrated in vacuo. The residue was purified by silica gel chromatography (Heptane/AcOEt: 85:15 to 1:1) leading to 3-O-benzoyl-N-palmitoyl-1-O-trityl-D-erythro-sphingosine (207 mg, 60%).
$^1$H NMR (400 MHz, CDCl$_3$): 0.88 (6H, t), 1.31-1.23 (46H, m), 1.56 (2H, m), 1.99 (2H, m), 2.08 (2H, t), 3.17 (1H, dd, J=7.4 Hz, J=3.9 Hz, CH(H')OH), 3.43 (1H, dd, J=9.7 Hz, 3.9 Hz, CH(H')OH], 4.47 (1H, m, CH— (NHCOR)), 5.43 [1H, dd, J=15.3 Hz, J=7.3 Hz, CH(OCOPh)CH═], 5.75-5.60 [2H, m, NH, CH(OCOPh)], 5.86 (1H, dt, J=15.3 Hz, J=7.9 Hz, CH$_2$CH═), 7.25-7.10 (9H, m), 7.40-7.30 (8H, m), 7.54 (1H, t, J=7.5 Hz), 7.92 (2H, d, J=7.3 Hz).
Deprotection at C1
A solution of 3-O-Benzoyl-N-palmitoyl-1-O-trityl-D-erythro-sphingosine (1.10 & 1.24 mmol) and p-toluene sulfonic monohydrate acid (0.23 g, 1.36 mmol) in a mixture of CH$_2$Cl$_2$ (18 ml) and methanol (18 ml) was placed under agitation 3 hours at ambient temperature. The reaction medium was concentrated in vacuo and re-dissolved in ethyl acetate (30 mL), washed with saturated aqueous NaHCO$_3$ solution, washed with brine (30 ml), dried over MgSO$_4$ and concentrated in vacuo. The residue was purified by silica gel chromatography (Heptane/AcOEt 1:1) leading to 3-O-Benzoyl-N-Palmitoyl-D-erythro-sphingosine (0.64 g; 80%) which is compound G.
$^1$H NMR (400 MHz, CDCl$_3$, CD$_3$OD): 0.87 (6H, t), 1.30-1.10 (46H, m), 1.54 (2H, m), 1.96 (2H, m), 2.14 (2H, m), 2.77 (2H, br s), 3.71 (2H, m, CH$_2$O), 4.24 (1H, m, CHN), 5.60-5.40 [2H, m, CH(OCOPh)C$\underline{H}$═], 5.79 (1H, dt, J=15.0 Hz, J=6.8 Hz, CH$_2$CH═), 6.18 (1H, d, J=9.6 Hz, NH), 7.38 (2H, dd, J=7.6 Hz, J=7.2 Hz), 7.52 (1H, dd, J=7.6, J=7.6 Hz), 7.96 (1H, d, J=7.2 Hz).

Example 5 According to the Invention: Synthesis of Compounds E, F and G According to the Invention Binding of the Fatty Chain of the Amide (Compound E):
To a suspension containing HBTU (3.30 g; 8.72 mmol), the ester hydrochloride salt obtained in Example 2 (3.0 g; 7.94 mmol) and palmitic acid (2.04 g; 7.94 mmol) in DMF (17 mL) and THF (106 mL), the dropwise addition was made of triethylamine (2.7 mL) at 0° C. The reaction medium was left under agitation 6 hours at ambient temperature. 120 ml of MTBE were added and the organic phase washed with brine (2×100 mL), dried over MgSO$_4$, filtered and concentrated in vacuo. The residual solid was purified by flash chromatography on silica gel and led to the ceramide in the form of a white solid (4.6 g; 100%).
Protection of the Alcohol at C3 (Compound F):
To a solution of ceramide ester (4.60 g; 8.72 mmol) and imidazole (1.56 g; 23.00 mmol) in DMF (35 mL) the dropwise addition was made of TBDMSCI (3.00 g; 19.83 mmol) in solution in 15 ml DMF. The reaction medium was left under agitation 60 h, at ambient temperature. 150 mL of MTBE and 150 ml of water were added. The organic phase was decanted and the aqueous phase extracted with MTBE (3×50 mL). The organic phases were then combined, washed with water (100 mL) then with brine (100 mL), dried over MgSO$_4$, filtered and concentrated in vacuo. The residual oil obtained was purified by flash chromatography on silica gel and led to the silylated ceramide (5.30 g; 96%). Compound F according to the invention was obtained.
Deprotection of the Alcohol at C1 (Synthesis of Compound G According to the Invention)
To a solution of silylated ceramide (1.50 g; 2.16 mmol) in anhydrous THF (15 mL), LiBH (11.9 mL; 2M In THF) was added dropwise. The system was left under agitation 24 hours at ambient temperature. 70 mL of CH$_2$Cl$_2$ were added and the reaction quenched through the addition of 70 ml saturated aqueous NH$_4$Cl solution. The organic phase was washed with brine (60 mL), dried over MgSO$_4$, filtered and concentrated in vacuo leading to a colourless oil. Purification on silica gel led to 3-O-tertbutyldimethylsilyl-N-palmitoyl-D-erythro-sphingosine (1.2 g; 85%) in the form of a white solid.

Comparison Between the Pathway of the Invention and the Prior Art Pathway:

Compound F obtained according to Examples 1, 2, 3 and 5 was obtained with a global molar yield of 23% from tetradecaldehyde. The yield of the same compound following the pathway known in the prior art was 3.2%. This evidences the importance of using the type E intermediate to access the precursors of sphingolipids F.

Example 6: Synthesis of a Sphingomyelin (from Compound G According to the Prior Art)

N-palmitoyl-D-erythro-sphingomyelin

To a solution of 3-O-t-butyldimethylsilyl-N-palmitoyl-D-erythro-sphingosine (0.5 g, 0.77 mmol) and TMEDA (0.12 mL, 0.81 mmol) in anhydrous toluene (12.5 ml) the dropwise addition was made of 2-chloro-2-oxo-1,3,2-dioxaphospholane (0.17 mL, 1.84 mmol) dissolved in 0.25 mL of acetonitrile. The reaction medium was left under agitation 3 hours at ambient temperature then transferred under argon into a sealed tube. 12.5 mL of acetonitrile then trimethylamine gas (3 mL) were successively added. The system was heated for 14 hours at 70° C., cooled and concentrated in vacuo.

The 3-O-tertbutyldimethylsilyl-N-palmitoyl-D-erythro-sphingomyelin was then dissolved in THF (5.0 mL) after which TBAF (1M in THF, 2.3 mL) was added. The mixture was heated 14 hours at 45° C. An additional 2.3 mL of TBAF were added. After 2 further hours at 45° C. the reaction was completed. The solution was concentrated in vacuo and dissolved in 15 mL of $CH_2Cl_2$, washed with water and concentrated in vacuo. The residue obtained was dissolved in 1 mL of $CH_2Cl_2$ and ? ml of MeOH. 7 mL of acetone were added and the system cooled 2 hours at 0° C. The precipitate formed corresponding to N-palmitoyl-D-erythro-sphingomyelin was filtered and vacuum dried (260 mg; 48% in 3 steps).

The invention claimed is:
1. Synthesis intermediates E' and F to access derivatives of sphingosine or ceramides, of general formulas:

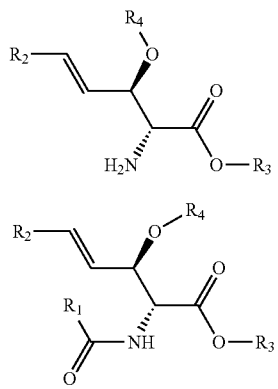

wherein
$R_1$ is a straight-chain or branched aliphatic chain of general formula $C_pH_{2p+1}O_r$, where p is an integer of between 8 and 35, and r is an integer of between 0 and 2;

$R_2$ is an aliphatic fatty chain of general formula $C_nH_{2n+1}$, n being an integer greater than or equal to 8 and less than or equal to 35;

$R_3$ is a radical having at least 1 carbon atom of alkyl, aryl, alkyl-aryl type optionally substituted; and $R_4$ is a protective group of the alcohol functions, wherein, the protective group is selected from the group consisting of benzyl, trityl, benzoyl, methoxymethyl, methoxyethyl, tetrahydropyryl, tri-alkyl silyl and alkyl-aryl silyl radical.

2. The intermediates according to claim 1 wherein p equals 15 and r is zero.

3. The intermediates according to claim 1 wherein n is an integer of between 10 and 20.

4. The intermediates according to claim 1 wherein n equals 13.

5. The intermediates according to claim 1 wherein $R_3$ is a carbon radical of alkyl type.

6. The intermediates according to claim 1 wherein $R_3$ is a methyl, ethylpropyl or isopropyl group.

7. The intermediates according to claim 1 wherein $R_4$ is a tri-alkyl silyl or alkyl-aryl silyl.

8. The intermediates according to claim 1 wherein $R_4$ is selected from the group consisting of trimethyl silyl, tert-butyl dimethysilyl, triethyl silyl, tri-isopropylsilyl, tert-butyldiphenyl silyl, dimethylphenyl silyl, and triphenyl silyl.

9. The intermediates according to claim 1 wherein $R_4$ is a tert-butyldimethyl silyl group.

10. A method of producing compounds of intermediate F from compound E' defined in claim 1, which comprises
mixing compound E' with a fatty acid R1C(O)OH in the presence of a peptide coupling agent.

11. A method of synthesizing molecules G of general formula:

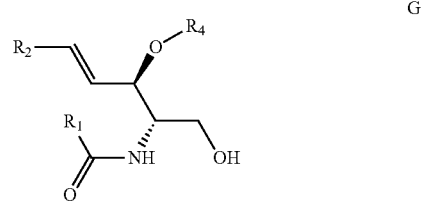

which comprises reducing the ester function of the C1 carbon of intermediate compound F of claim 1 to a primary alcohol.

12. The method according to claim 11, wherein the reduction of the ester function of the C1 carbon of intermediate compound F is performed using lithium borohydride.

13. A method to convert E' to F which comprises:
reacting intermediate compound E' according to claim 1 with the fatty acid R1C(O)OH in the presence of a peptide coupling agent selected from the group consisting of carbodiimides, benzotrialzoles and mixtures thereof, in an aprotic polar solvent selected from the group consisting of DMF, THF and mixtures thereof, wherein the reaction is held under agitation at a temperature between 20 and 70° C. until disappearance of the intermediate compound E' and fatty acid.

14. The method according to claim 13 wherein the peptide coupling agent is N,N,N',N'-tetramethyl-O-(1H-benzotriazol-1-yl) uronium hexafluorophosphate (HBTU).

15. A method of producing compounds of intermediate F from compound E, which comprises reacting compound E with a reagent carrying an alcohol function protecting group

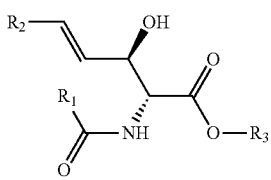

E

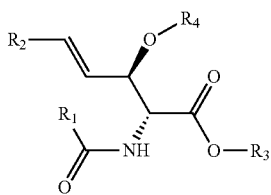

F wherein $R_1$ is a saturated or unsaturated carbon fatty chain optionally substituted with oxygen;

$R_2$ is an aliphatic fatty chain of general formula $CnH_{2n+1}$, n being an integer greater than or equal to 8 and less than or equal to 35;

$R_3$ is a radical having at least 1 carbon atom of alkyl, aryl, alkyl-aryl type optionally substituted;

$R_4$ is a protective group of the alcohol functions, wherein, the protective group is selected from the group consisting of benzyl, trityl, benzoyl, methoxymethyl, methoxyethyl, tetrahydropyryl, tri-alkyl silyl and alkyl-aryl silyl radical; and the alcohol function protecting group of the reagent is selected from the group consisting of benzyl, trityl, methoxymethyl, methoxyethyl, dihydropyryl, trimethyl silyl, tert-butyl dimethyl silyl, triethyl silyl, tri-isopropylsilyl, tert-butyldiphenyl silyl, dimethylphenyl silyl, and triphenyl silyl.

16. The method according to claim 15, wherein the reaction is conducted in a polar solvent selected from the group consisting of dimethyl formamide, dichloroethane and acetonitrile, at a temperature ranging from 25 to 90° C. until complete disappearance of the intermediate compound E; and adding a non-nucleophilic weak base to the reaction.

17. The method according to claim 15, wherein the reagent carrying an alcohol function protecting group is selected from the group consisting of a halide of benzyl, trityl, methoxymethyl, methoxyethyl, dihydropyryl, trimethyl silyl, tert-butyl dimethyl silyl, triethyl silyl, tri-isopropylsilyl, tert-butyldiphenyl silyl, dimethylphenyl silyl, and triphenyl silyl.

18. The method according to claim 17 wherein the alcohol protecting reagent is tert-butyldimethyl silyl chloride.

19. The method according to claim 16 wherein the non-nucleophilic weak base is selected from the group consisting of imidazole, pyridine, diisopropylamine, diisopropylethyl amine (DIPEA), dimethylamino pyridine (DMAP) and triethyl amine.

20. The method according to claim 16 wherein the polar solvent is dimethyl formamide and the temperature is between 20 and 70° C.

* * * * *